(12) United States Patent
Yoshioka et al.

(10) Patent No.: US 6,635,798 B1
(45) Date of Patent: Oct. 21, 2003

(54) LAMINATED PANEL

(75) Inventors: Toshiyasu Yoshioka, Kagawa-ken (JP); Yuka Miyazaki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/669,146

(22) Filed: Sep. 27, 2000

(30) Foreign Application Priority Data

Sep. 29, 1999 (JP) .......................................... 11-275848

(51) Int. Cl.[7] .............................................. A61F 13/15
(52) U.S. Cl. ................... 604/365; 604/372; 604/385.01
(58) Field of Search ..................... 604/385.01, 385.04, 604/385.24, 385.25, 365, 372; 428/369, 373, 397; 118/241, 323, 674, 681; 427/207.1, 208.2, 208.4, 208.6, 284, 285

(56) References Cited

U.S. PATENT DOCUMENTS

| | | | | |
|---|---|---|---|---|
| 3,720,554 A | * | 3/1973 | Stumpf ....................... 156/62.6 |
| 4,764,234 A | * | 8/1988 | Smits et al. ................. 156/164 |
| 4,960,619 A | * | 10/1990 | Slautterback et al. ........ 427/265 |
| 5,026,450 A | * | 6/1991 | Cucuzza et al. ........ 156/244.11 |
| 5,064,492 A | * | 11/1991 | Friesch ........................ 156/191 |
| 5,334,176 A | * | 8/1994 | Buenger et al. ............. 604/367 |
| 5,342,647 A | * | 8/1994 | Heindel et al. .............. 47/2.31 |
| 5,662,991 A | * | 9/1997 | Smolik et al. .............. 442/319 |
| 5,932,284 A | * | 8/1999 | Reynolds .................... 427/207 |
| 6,049,023 A | * | 4/2000 | Blenke et al. .............. 604/368 |
| 6,123,694 A | * | 9/2000 | Pieniak et al. ........... 604/385.2 |
| 6,143,818 A | * | 11/2000 | Wang et al. ................ 524/528 |
| 6,171,290 B1 | * | 1/2001 | Boisse et al. .......... 604/385.01 |

* cited by examiner

Primary Examiner—Weilun Lo
Assistant Examiner—Jacqueline F Stephens
(74) Attorney, Agent, or Firm—Clark & Brody

(57) ABSTRACT

A laminated panel including at least two sheet members which are overlapped with and joined to each other with adhesives B1 to B4 applied on at least one of inner surfaces of the sheet members. The adhesives B1 to B4 form a plurality of separated adhesive lines L extending in one direction while being bent; the number of times in which one of the adhesive lines L repeats bending is in the range of 50 to 200 per 1 m of dimension of the sheet members; and the number of times in which one of the adhesive lines L intersects is in the range of 0 to 200 per 1 m of dimension of the sheet members.

3 Claims, 4 Drawing Sheets

LAMINATED PANEL

BACKGROUND OF THE INVENTION

The present invention relates to a laminated panel comprising at least two sheet members, and in particular to a laminated panel for a diaper cover, disposable diaper, sanitary napkin, urine-absorbent pad and the like.

Japanese Patent Application Disclosure No. 1996-196559 discloses a disposable diaper comprising a liquid-permeable topsheet, a liquid-impermeable backsheet and a liquid-absorbent core interposed between the topsheet and the backsheet. The core formed of a liquid retaining layer and a fiber assembled layer is covered with tissue paper (water-permeable sheet), and the core and the tissue paper are joined by means of hotmelt adhesive substantially in the entire area of the surface at which the core and the tissue paper overlap with each other. The application pattern of the adhesive includes a dot-like application pattern formed with a plurality of straight continuous dot-like lines extending in one direction; a vertical stripe application pattern formed with a plurality of straight lines extending in one direction; a grid-like application pattern formed with straight lines extending while intersecting with each other; and a spiral application pattern formed with a plurality of curved lines extending while intersecting with themselves.

SUMMARY OF THE INVENTION

The adhesive applied in the dot-like pattern or the vertical stripe pattern can prevent delamination between the core and the tissue paper with respect to the direction perpendicular to the direction in which the adhesive extends. However, with respect to the direction in which the adhesive extends, delamination between the core and the tissue paper is prevented just at points, so that the core and the tissue paper may easily be delaminated in the direction in which the adhesive extends.

In order to reinforce the adhesive strength, it is preferable to apply the adhesive in the grid-like pattern or in the spiral pattern. However, at the points where the adhesive intersects with other adhesive or itself, the adhesive is applied one upon another, resulting that the application amount of the adhesive is increased compared to the portion where the adhesive does not intersect with other adhesive or itself. At the intersecting points, the adhesive having soaked into the tissue paper will close fiber gaps of the tissue paper over a wide area. Accordingly, if the number of intersecting points is too large, the adhesive will sometimes prevent the liquid permeability of the tissue paper.

It is an object of the invention to provide a laminated panel in which an adhesive is applied so that delamination is unlikely to occur in a direction in which the adhesive extends as well as in a direction intersecting the direction comprising the adhesive extends, and liquid permeability possessed by sheet members will not be prevented.

A laminated panel of the present invention comprises at least two sheet members overlapped with and joined to each other by means of adhesive applied on at least one of inner surfaces of the sheet members, wherein the adhesive forms a plurality of separated adhesive lines extending in one direction while being bent; the number of times in which one of the adhesive lines repeats bending is in the range of 50 to 200 per 1 m of the sheet member; the number of times in which one of the adhesive lines intersects is in the range of 0 to 200 per 1 m of the sheet member.

In the present invention "bending" or "bent" involves the case where the adhesive line extends in a zigzag pattern while being bent; the case where the adhesive line extends in a wave shape while rising and falling; and the case where the adhesive line extends in a square wave shape while picturing bumps and dips.

In the laminated panel constituting the body fluid disposal article, since the adhesive does not prevent the liquid permeability of the topsheet and the water permeability of the tissue paper, body fluids can be smoothly transferred from the topsheet to the tissue paper, and then from the tissue paper to the core, with the result that it is possible to sufficiently utilize the liquid absorptivity possessed by the core.

DETAILED DESCRIPTION OF PREFERRED EMBODIMENT

In the following, with reference to the accompanied drawings, a laminated panel according to the present invention will be described in more detail by taking a disposable diaper as an example.

Figure 1:
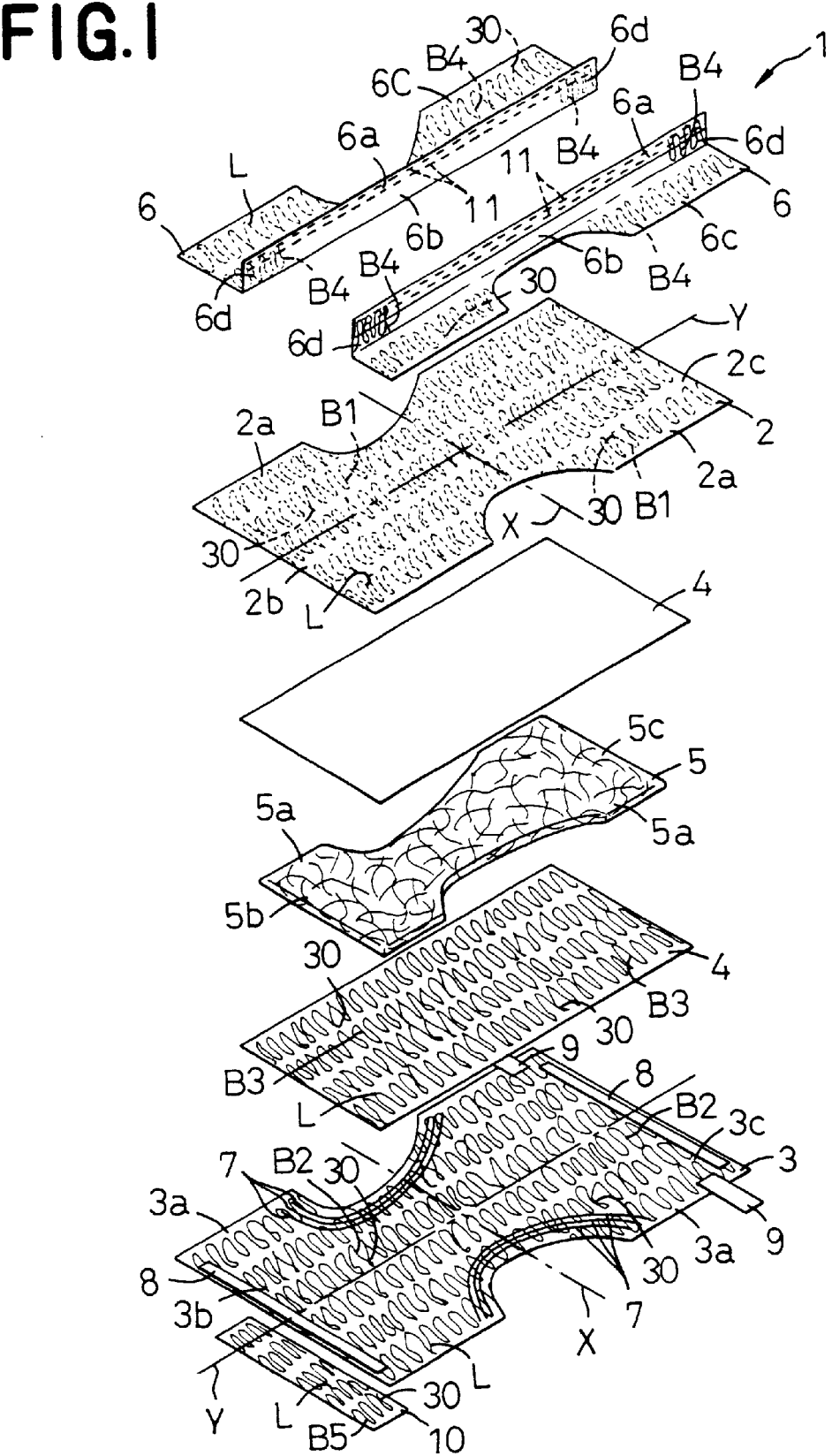
FIG. 1 is an exploded perspective view of a disposable diaper.

FIG. 1 is an exploded perspective view of a disposable diaper 1. The diaper 1 comprises a liquid-permeable topsheet 2 of hourglass shape, a liquid-impermeable backsheet 3 of hourglass shape, a pair of tissue papers 4 (liquid-permeable sheets) interposed between the topsheet 2 and the backsheet 3, a liquid-absorbent core 5 of hourglass shape interposed between the tissue papers 4, and a pair of liquid-barrier sheets 6 opposed to and spaced from each other and extending in the vertical direction.

The diaper 1 has, in addition to the above constituents of the diaper 1, a pair of leg encirclable elastic members 7 opposed to and spaced from each other and extending in the vertical direction, a pair of waist encirclable elastic members 8 opposed to and spaced from each other and extending in the horizontal direction, a tape fastener 9 and a target tape 10 serving as a receiving area of the tape fastener 9. In the drawing, the barrier sheets 6 are disposed at the top, then the topsheet 2, the tissue paper 4, the core 5, the tissue paper 4, the backsheet 3 and the target tape 10 are disposed in this order toward the bottom of the drawing.

The topsheet 2 and the backsheet 3 have both side edges 2a and 3a, the respective both side edges opposed to each other and extending in the vertical direction, and front and back end edges 2b, 2c and 3b, 3c, the respective front and back end edges opposed to each other and extending in the horizontal direction. The respective both side edges 2a and 3a of the topsheet 2 and the backsheet 3 are angularly recessed at their center portions toward a vertical center line Y separating the topsheet 2 and the backsheet 3 into two halves in the horizontal direction, and the recesses are large on the side of the front end edges 2b and 3b with respect to a horizontal center line X separating the topsheet 2 and the backsheet 3 into two halves in the vertical direction, while the recesses are smaller on the side of the back end edges 2c and 3c compared to the side of the front end edges 2b and 3b. Therefore, the topsheet 2 and the backsheet 3 are formed larger in size on the side of the back end edges 2c and 3c than the side of the front end edges 2b and 3b.

On the inner surface of the backsheet 3, the pair of leg encirclable elastic members 7 which are elastically extensible along the both side edges 3a of the backsheet 3 are arranged, and the pair of film-like waist encirclable elastic members 8 which are elastically extensible along the front and back end edges 3b, 3c of the backsheet 3 are arranged in elongated state.

On the inner surface of the backsheet 3 on the side of the back end edge 3c, a proximal end of the tape fastener 9 extending inwardly in the horizontal direction from the both side edges 3a of the backsheet 3 is arranged.

The tissue paper 4 is of a rectangular shape having an area smaller than those of the topsheet 2 and the backsheet 3 but larger than that of the core 5.

The barrier sheet 6 has free side edge portions 6a extending in the vertical direction, base side edge portions 6b opposed to the free side edge portions 6a and extending in the vertical direction, outside portions 6c protruding outwardly in the horizontal direction from the base side edge portions 6b and extending in the vertical direction, and both end portions 6d in the vertical direction located at the front and back end edges 2b, 2c and 3b, 3c of the topsheet 2 and the backsheet 3. On the free side edge portions 6a of the barrier sheets 6, elastic extensible members 11 are mounted in elongated state while being covered with the free side edge portions 6a. The outside portions 6c of the barrier sheets 6 are angularly recessed at their center portions inwardly in the horizontal direction.

On the inner surfaces of the topsheet 2 and the backsheet 3 opposed to each other, adhesives B1 and B2 are applied for joining the topsheet 2 and the backsheet 3 and joining the topsheet 2 and the backsheet 3 to the tissue paper 4. On the inner surface of the tissue paper 4 in the lower portion of the drawing, an adhesive B3 is applied for adhering the tissue paper 4 and the core 5. On the inner surfaces of the barrier sheets 6 at the outside portions 6c and on the outer surfaces of the barrier sheets 6 at the both end portions 6d, adhesives B4 are applied for joining the outside portions 6c of the barrier sheets 6 to the topsheet 2 and the backsheet 3, and the adhesives B4 are applied for joining the both end portions 6d of the barrier sheets 6 to the outside portions 6c of the barrier sheet 6. On the inner surface of the target tape 10, an adhesive B5 is applied for joined the target tape 10 to the outer surface of the backsheet 3. On the proximal end of the tape fastener 9 is applied an adhesive (not shown), so that it is adhered to the backsheet 3.

The adhesives B1 to B5 form a plurality of separated adhesive lines L extending in the vertical direction of the diaper 1 while raising and falling in wave shapes. In the adhesive lines L, adjacent adhesive lines L extend so as not to intersect with each other, and intersecting points 30 where a certain adhesive line L intersects with itself are dispersed.

The adhesives B1 to B5 are applied on the topsheet 2, the backsheet 3, the tissue paper 4, the barrier sheet 6 and the target tape 10 substantially uniformly so as to eliminate unevenness.

In the drawing, by covering the entire core 5 with the tissue paper 4, the core 5 and the tissue paper 4 are joined to each other by means of the adhesive B3 applied on the tissue paper 4. The tissue paper 4 and the tissue paper 4 are joined to each other at the part extending outwardly in the circumferential direction of the core 5 from the periphery of the core 5. By overlaying the topsheet 2 and the backsheet 3 on the outer surfaces of the respective tissue papers 4, the tissue papers 4 are joined to the topsheet 2 and the backsheet 3 by means of the adhesives B1 and B2 applied on the topsheet 2 and the backsheet 3, while the topsheet 2 and the backsheet 3 are joined to each other at the both side edges 2a and 3a and the front and back end edges 2b, 2c and 3b, 3c of the topsheet 2 and the backsheet 3.

By overlaying the outside portions 6c of the barrier sheets 6 on the both side edges 2a and 3a of the topsheet 2 and the backsheet 3, and overlaying the both end portions 6d of the barrier sheets 6 on the outside portions 6c of the barrier sheets 6 while being fallen down to the outside of the diaper 1, the outside portions 6c of the barrier sheets 6 are joined to the both side edges 2a and 3a of the topsheet 2 and the backsheet 3 via the adhesives B4 applied on the outside portions 6c of the barrier sheets 6, and the both end portions 6d of the barrier sheets 6 are joined to the outside portions 6c of the barrier sheets 6 by means of the adhesives B4 applied on the both end portions 6d of the barrier sheets 6. By overlaying the inner surface of the target tape 10 on the outer surface of the backsheet 3 at the front end edge 3a, the target tape 10 is joined to the backsheet 3 by means of the adhesive B5 applied on the target tape 10.

Figure 2:
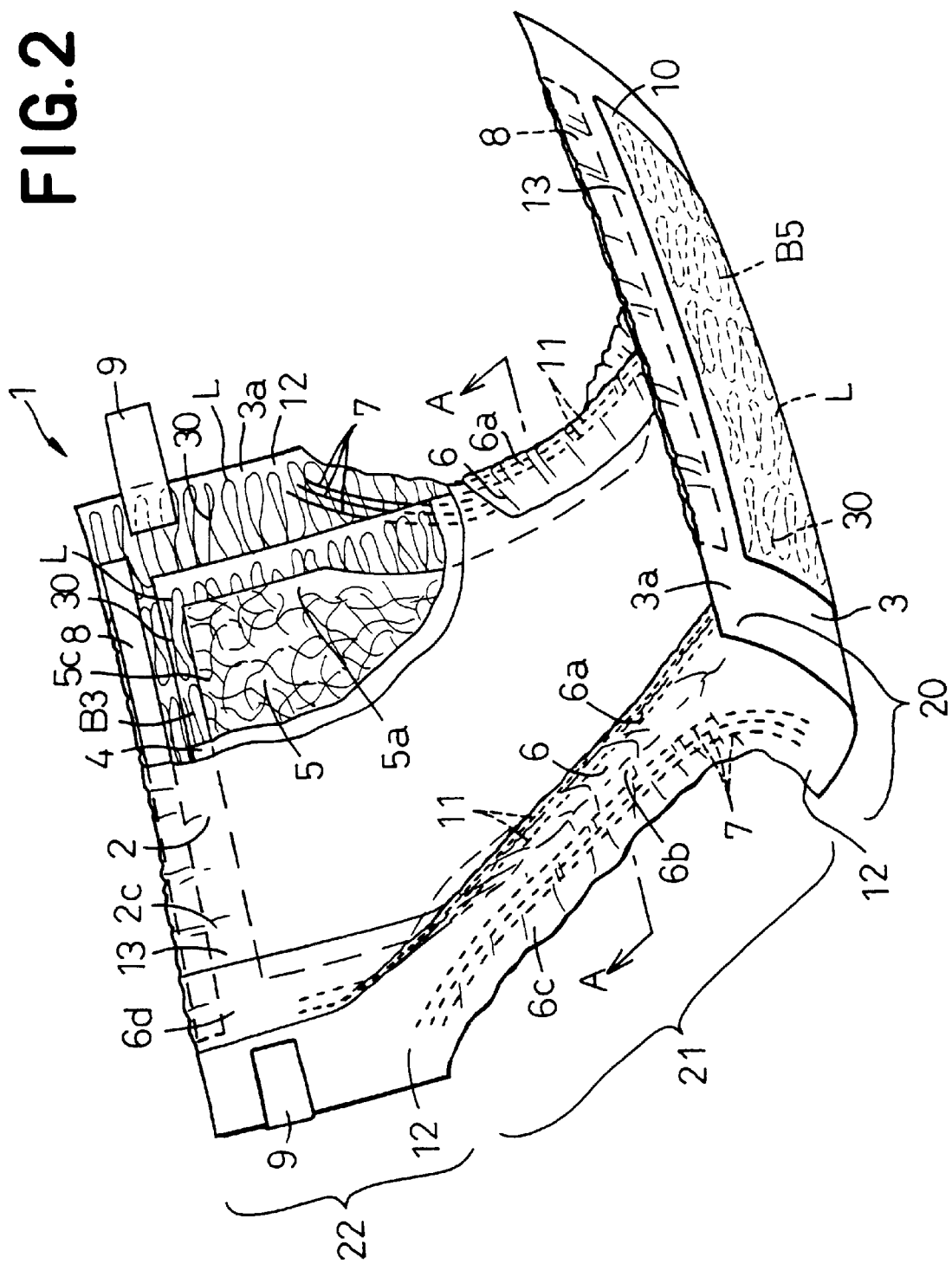
FIG. 2 is a partially cutaway perspective view of a diaper in assembled state.
Figure 3:
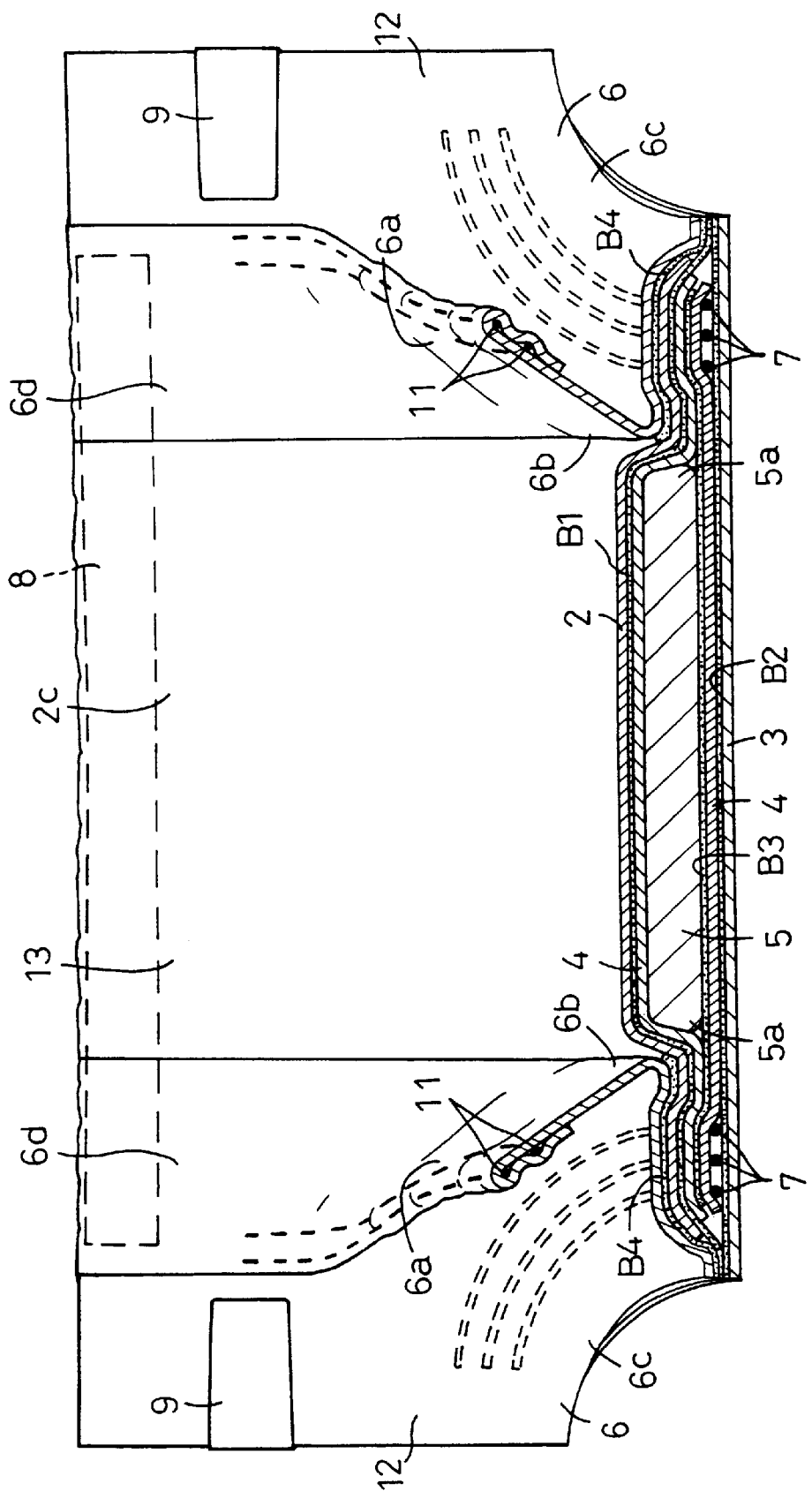
FIG. 3 is a section view along line A—A of FIG. 2.

FIG. 2 is a partially cutaway perspective view of the diaper 1 in a state that the exploded perspective view of FIG. 1 is assembled, and FIG. 3 is a section view taken in the direction of the arrows along line A—A. The diaper 1 has a front waist region 20, a back waist region 22 and a crotch region 21 located between the front waist region 20 and the back waist region 22, and further has a pair of side flaps 12 opposed to each other and extending in the vertical direction, the side flaps 12 being recessed inwardly in the horizontal direction of the diaper 1 in the crotch region 21, and a pair of end flaps 13 opposed to each other and extending in the horizontal direction.

The side flaps 12 are formed of the both side edges 2a and 3a of the topsheet 2 and the backsheet 3, and the outside portions 6c of the barrier sheets 6. In the side flaps 12, the both side edges 2a of the topsheet 2 extend outwardly in the horizontal direction from both side edges 5a of the core 5, and the both side edges 3a of the backsheet 3 and the outside portions 6c of the barrier sheets 6 extend outwardly in the horizontal direction from the both side edges 2a of the topsheet 2. In the side flaps 12, the both side edges 2a and 3a of the topsheet 2 and the backsheet 3 are joined by means of the adhesives B1 and B2, and the both side-edges 2a and 3a of the topsheet 2 and the backsheet 3 and the outside portions 6c of the barrier sheets 6 are joined by means of the adhesives B2 and B4. In the side flaps 12, the leg encirclable elastic members 7 are joined to the inner surface of the backsheet 3 while being interposed between the tissue paper 4 and the backsheet 3.

The end flaps 13 are formed of the front and back end edges 2b, 2c and 3b, 3c of the topsheet 2 and the backsheet 3, and part of the outside portions 6c and the both end portions 6d of the barrier sheets 6. In the end flaps 13, the front and back end edges 2b, 2c and 3b, 3c of the topsheet 2 and the backsheet 3 are joined and the front and back end edges 2b, 2c of the topsheet 2 are joined to part of the outside portions 6c of the barrier sheets 6. In the end flaps 13, the both end portions 6d of the barrier sheets 6 are joined to the outside portions 6c of the barrier sheets 6, and the waist encirclable elastic members 8 are joined to the inner surfaces of the topsheet 2 and the backsheet 3 while being interposed between the topsheet 2 and the backsheet 3.

In the back waist region 22 of the diaper 1, the tape fastener 9 is bent so as to extend inwardly in the horizontal direction of the diaper 1, the tape fastener 9 being removably adhered to the outer surface of the topsheet 2 by means of the adhesive (not shown) applied on the free end portion of the tape fastener 9. In the diaper 1, the side traps 12, the end traps 13 and the free side edge portions 6a of the barrier sheets 6 are formed with gathers under the condition that the elastic members 7, 8 and 11 are released from elongated state and the elastic members 7, 8 and 11 are in contracted state. In the diaper 1, the elastic members 11 attached to the free side edge portions 6a of the barrier sheets 6 are contracted, and the free side edge portions 6a of the barrier sheets 6 stand in an upward direction of the diaper 1.

As shown in FIG. 3, in the diaper 1, the adhesives B1 to B4 applied on the backsheet 3, the tissue papers 4 and the barrier sheets 6 do not appear such that they are dispersed in the horizontal direction of the diaper 1, but the adhesives B1 to B4 extending with being bent appear such that they are applied on generally whole areas of the topsheet 2, the backsheet 3, the tissue papers 4 and the barrier sheets 6 in the horizontal direction of the diaper 1. Therefore, the topsheet 2, the backsheet 3, the tissue papers 4 and the barrier sheets 6 are unlikely to delaminate not only in the horizontal direction of the diaper 1 but also in the vertical direction of the diaper 1.

In the side flaps 12, since the both side edges 3a of the backsheet 3 and the outside portions 6c of the barrier sheets 6 extend outwardly in the horizontal direction than the both side edges 2a of the topsheet 2, even when body fluids soak into the both side edges 2a of the topsheet 2, they cannot soak into the backsheet 3 and the barrier sheets 6, so that it is possible to prevent the body fluids from leaking from the side flaps 12.

Figure 4:
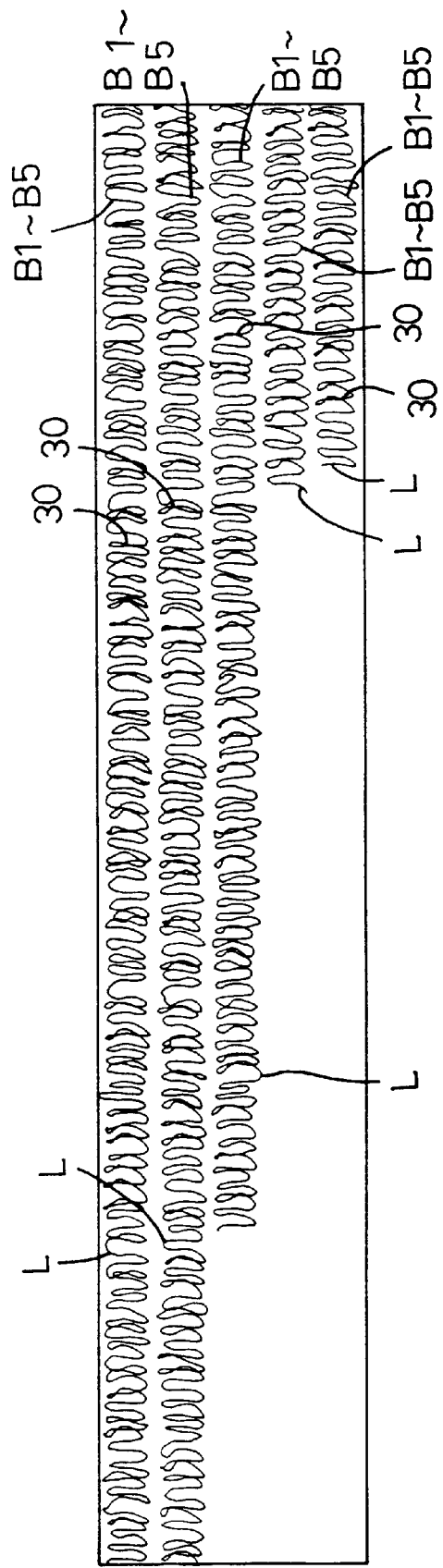
FIG. 4 is a view showing adhesive lines of an adhesive applied on a sheet member.

FIG. 4 shows adhesive lines L of the adhesives B1 to B5 applied on any one of the sheet members of the topsheet 2, the backsheet 3, the tissue papers 4, the barrier sheets 6 and the target tape 10, and the adhesives B1 to B5 are partially omitted in the drawing. The number of times in which one of the adhesive lines L repeats bending is in the range of 50 to 200, preferably in the range of 100 to 150 per 1 m of vertical dimension of the sheet member, and the number of times in which one of the adhesive lines L intersects is in the range of 0 to 200 per 1 m of vertical dimension of the sheet member. The number of times in which the adhesive line L repeats bending is counted by defining the part from the apex of the top to the apex of the neighboring top as one. The situation "the adhesive line L intersects" also involves the case where the adhesive line L contact with itself, in addition to the case where the adhesive line L intersects with itself.

If the number of times in which the adhesive line L repeats bending is less than 50, the interval between neighboring tops becomes large and the adhesive line approaches a straight line, resulting that adhesive strength of the adhesive in the direction in which the adhesive line L extends becomes weak. Contrarily, if the number of times in which the adhesive line L repeats bending is more than 200, there is a possibility that the number of times in which the adhesive line L intersects with itself exceeds 200.

At the points 30 where the adhesive line L intersects with itself, the adhesives B1 and B3 having soaked into the topsheet 2 and the tissue papers 4 close fiber gaps of the topsheet 2 and the tissue paper 4 over wide areas. Therefore, if the number of times in which the adhesive line L intersects with itself is more than 200, the liquid permeability of the topsheet 2 and the tissue paper 4 will be prevented. As a result, because the body fluids can not smoothly move from the topsheet 2 to the tissue paper 4, and then from the tissue paper 4 to the core 5, it is impossible to sufficiently utilize the liquid absorptivity of the core 5. Furthermore, even if the adhesive B3 does not soak into the tissue paper 4, the adhesive B3 extends on the inner surface of the tissue paper 4 to cover the surface of the core 5 at the points 30 where the adhesive line L intersects with itself, resulting that the liquid absorptivity of the core 5 will sometimes be prevented.

Preferably, in the case of adhering the topsheet 2 and the backsheet 3, the amounts of adhesives B1 and B2 to be applied on the topsheet 2 and the backsheet 3 are in the range of 3 to 8 g per 1 $m^2$ of area of the topsheet 2 and the backsheet 3; in the case of adhering the core 5 and the tissue paper 4, the amount of adhesive B3 to be applied on the tissue paper 4 is in the range of 0.8 to 5 g per 1 $m^2$ of area of the tissue paper 4; in the case of adhering the barrier sheets 6 to the topsheet 2 and the backsheet 3, the amount of adhesives B4 to be applied on the barrier sheets 6 is in the range of 3 to 8 g per 1 $m^2$ of area of the barrier sheet 6; and in the case of joining the topsheet 2 and the backsheet 3 to the elastic members 7 and 8, the amounts of adhesives B1 and B2 to be applied on the topsheet 2 and the backsheet 3 are in the range of 8 to 15 g per 1 $m^2$ of area of the topsheet 2 and the backsheet 3.

If the application amounts of the adhesives B1 to B5 are less than the above ranges, adhesive strength will become weak, so that the topsheet 2, the backsheet 3, the tissue papers 4, the barrier sheets 6, the core 5 and the elastic members 7 and 8 tend to easily delaminate in the adhering regions. If the application amounts of the adhesives B1 and B3 are more than the above ranges, the adhesives B1 and B3 having soaked into the topsheet 2 and the tissue paper 4 will close fiber gaps of the topsheet 2 and the tissue paper 4 over wide areas, resulting that the liquid permeability of the topsheet 2 and the water permeability of the tissue paper 4 are prevented, though this phenomenon depends on the basis weight and the fineness of the fiber forming the topsheet 2 or the tissue paper 4.

It is preferable that Viscosity numbers of the adhesives B1 to B5 are in the range of 4000 to 5500 cP. If the viscosity numbers of the adhesives B1 and B3 are less than 4000 cP, the adhesives B1 and B3 are likely to soak into the topsheet 2 and the tissue paper 4, and likely to expand inside of the fibers of the topsheet 2 and the tissue paper 4. Contrarily, if the viscosity numbers of the adhesives B1 to B5 are larger than 5500 cP, there is a possibility that the adhesives B1 to B5 solidify in clusters.

For the topsheet 2, a hydrophobic nonwoven fabric treated with a hydrophilic agent or a hydrophilic nonwoven fabric formed of fibers into which a hydrophilic agent is kneaded is used. For the backsheet 3 and the barrier sheet 6, a synthetic resin film or a laminated sheet of a synthetic resin film and a hydrophobic nonwoven fabric, and preferably a breathable liquid-impermeable sheet is used. As the nonwoven fabric, an air through nonwoven fabric, a point bonded nonwoven fabric, a span bonded nonwoven fabric, a span lace nonwoven fabric, a melt blown nonwoven fabric and the like can be used.

The core 5 is formed of a mixture of fluff pulp and high adsorbent polymer particles to which fibers are appropriately added for maintaining the shape of the absorber, and compressed into a predetermined thickness. For the liquid-permeable sheet covering the core 5, liquid-permeable non-woven fabrics having a basis weight in the range of 5 to 10 $g/m^2$ may be used besides the tissue paper 4.

For the elastic members 7, 8 and 11, elastomers such as synthetic rubber and natural rubber or materials in which such elastomers are adhered in elongated state to nonwoven fabrics may be used.

For the adhesives B1 to B5, block rubber hotmelt adhesives, olefinic hotmelt adhesives may be used. The adhesives B1 and B2 may be applied on either one of the topsheet 2 and the backsheet 3, besides the case where the adhesives B1 and B2 are applied on both of the topsheet 2 and the backsheet 3. Furthermore, the adhesives B1 to B5 may be applied in a dotted pattern. As for the barrier sheet 6, the both end portions 6c of the barrier sheets 6 may be adhered to the front and back end edges 2b, 2c of the topsheet 2 in a state that the both end portions 6c are fallen down to the inside of the diaper 1. In the case where the barrier sheets 6 are joined in a condition that the both end portions 6c are fallen down to the inside of the diaper 1, the adhesives B4 are applied on the inner surfaces of the barrier sheets 6 in the both end portions 6c.

The present invention may be applied to a diaper cover, sanitary napkin, urine-absorbent pad and the like, or to a composite sheet for dirt wiping or a composite sheet in which an extensible sheet is joined in elongated state to a non-extensible sheet and the like, in addition to the disposable diaper 1.

According to a laminated panel of the present invention, since the adhesives are applied on the sheet members so as to form a plurality of separated adhesive lines extending in one direction while being bent, it is possible to join the sheet members with substantially equal adhesive strength with respect to both of the direction in which the adhesive extends and the direction perpendicular to the direction in which the adhesive extends, so that delamination of the sheet members can be prevented.

Regarding the adhesive line, since the number of times in which the adhesive line repeats bending is in the range of 50 to 200 per 1 m of dimension of the sheet member, and the number of times in which the adhesive line intersects with itself is in the range of 0 to 200 per 1 m of dimension of the sheet member, even when the applied adhesive soaks into the sheet member and fiber gaps of the sheet member are closed, it is possible to suppress the area in which the fiber gaps are closed to minimum, so that the liquid permeability and water permeability of the sheet material will not be prevented.

In the case where the application amount of the adhesive is in the range of 0.8 to 8 g per 1 $m^2$ of area of the sheet member, it is possible to prevent the adhesive having soaked into the sheet member from closing the fiber gaps of the sheet member over wide areas while preventing delamination of the sheet member.

What is claimed is:

1. A laminated panel comprising at least two sheet members overlapped with and joined to each other by means of an adhesive applied on at least one of inner surfaces of the sheet members, wherein the adhesive forms a plurality of separated adhesive lines extending in one direction, each of the separated adhesive lines bending in a generally zigzag pattern in the one direction; the number of times in which one of the adhesive lines repeats bending is in the range of 50 to 200 per 1 m of dimension of the sheet member and the number of times in which one of the adhesive lines intersects is in the range of 0 to 200 per 1 m of dimension of the sheet member, wherein the two sheet members are a liquid-permeable topsheet and a liquid-impermeable backsheet, and a liquid-absorbent core is interposed therebetween to constitute a disposable body fluid article and the topsheet, the backsheet and the core are joined to one another by means of the adhesive applied on at least one of inner surfaces of the topsheet and backsheet;

wherein the panel also comprises:

a water-permeable inner sheet interposed between the topsheet and the backsheet to cover the surface of the core and the core and the water-permeable inner sheet are joined to each other by means of the adhesive applied on the inner surface of the water-permeable inner sheet opposing to the core, a pair of side flaps extending in a vertical direction thereof on an outside of both side edges of the core;

a pair of end flaps extending in a horizontal direction thereof on an outside of both end edges of the core; the side flaps and the end flaps are formed in at least a part of the topsheet and the backsheet;

a pair of leg encirclable elastic members are arranged in the side flaps the elastic members extending in a leg encirclable and elastically extensible;

a waist encirclable elastic member is arranged in at least one of the end flaps, the elastic member extending in the horizontal direction and elastically extensible; and the leg encirclable elastic members and the waist encirclable elastic member are joined to at least one of inner surfaces of the topsheet and the backsheet by means of adhesive in an extended state; and wherein the amount of adhesive used to adhere the topsheet to the backsheet is in the range of 3–8 $g/m^2$, the amount of adhesive used to adhere the core to the water-permeable inner sheet is in the range of 0.8 to 5 $g/m^2$, and the amount of adhesive used to adhere the leg encirclable elastic members and the waist encirclable elastic member to the topsheet and the backsheet is in the range of 8–15 $g/m^2$.

2. The panel according to claim 1, wherein the article comprises a pair of liquid-resistant barrier sheets extending in the vertical direction in vicinity of the both side edges of the core and having rising orientation in upward direction of the article under elastic extension; outside portions of the barrier sheets located at the side flaps and extending in the vertical direction are joined to the side flaps by means of the adhesive applied on at least one of inner surfaces of outside portions of the barrier sheet, an outer surface of the topsheet and an outer surface of the backsheet; both end portions in the vertical direction of the barrier sheets located at the end flaps are joined to the end flaps by means of adhesive applied on at least one of the both end portions of the barrier sheets, the outer surface of the topsheet and the outer surface of backsheet while being fallen down inwardly in the horizontal direction or outwardly in the vertical direction of the article.

3. The panel according to claim 2, wherein an amount of adhesive used to secure the topsheet to the backsheet and the barrier sheet to the topsheet and backsheet is in the range of 3–8 $g/m^2$.

* * * * *